(12) United States Patent
Kosemund et al.

(10) Patent No.: US 7,414,043 B2
(45) Date of Patent: Aug. 19, 2008

(54) 9-α-SUBSTITUTED ESTRATRIENES AS SELECTIVELY ACTIVE ESTROGENS

(75) Inventors: Dirk Kosemund, Erfurt (DE); Gerd Mueller, Jena (DE); Alexander Hillisch, Jena (DE); Karl-Heinrich Fritzemeier, Berlin (DE); Peter Muhn, Berlin (DE)

(73) Assignee: Schering AG, Berlin (DE)

( * ) Notice: Subject to any disclaimer, the term of this patent is extended or adjusted under 35 U.S.C. 154(b) by 267 days.

(21) Appl. No.: 10/458,735

(22) Filed: Jun. 11, 2003

(65) Prior Publication Data

US 2004/0087565 A1     May 6, 2004

Related U.S. Application Data

(60) Provisional application No. 60/443,868, filed on Jan. 31, 2003.

(30) Foreign Application Priority Data

Jun. 11, 2002   (DE)   ................ 102 26 326

(51) Int. Cl.
*A61K 31/56* (2006.01)
*C07J 1/00* (2006.01)

(52) U.S. Cl. .............. 514/182; 552/624; 514/825; 514/843

(58) Field of Classification Search ............. 514/182; 55/624; 552/624
See application file for complete search history.

(56) References Cited

U.S. PATENT DOCUMENTS 3,960,841 A    6/1976   Yukishige et al.

FOREIGN PATENT DOCUMENTS

DE    19906159    8/2000

*Primary Examiner*—Barbara P Badio
(74) *Attorney, Agent, or Firm*—Millen, White, Zelano & Branigan, P.C.

(57) ABSTRACT

This invention describes the new 9α-substituted estratrienes of general formula I

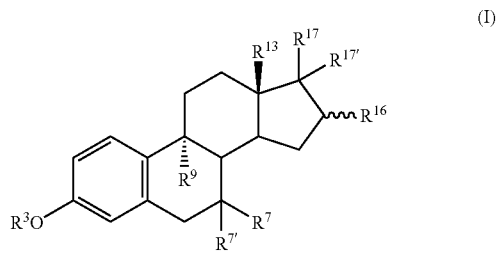

in which $R^3$, $R^7$, $R^{7'}$, $R^{13}$, $R^{16}$ as well as $R^{17}$ and $R^{17'}$ have the meanings that are indicated in the description and $R^9$ means a straight-chain or branched-chain, optionally partially or completely halogenated alkenyl radical with 2 to 6 carbon atoms, an ethinyl or prop-1-inyl radical, as pharmaceutical active ingredients that exhibit in vitro a higher affinity to estrogen receptor preparations from rat prostates than to estrogen receptor preparations from rat uteri and in vivo preferably a preferential action on the ovary in comparison to the uterus, their production, their therapeutic use and pharmaceutical dispensing forms that contain the new compounds.

The invention also describes the use of these compounds for treating estrogen-deficiency-induced diseases and conditions.

26 Claims, 2 Drawing Sheets

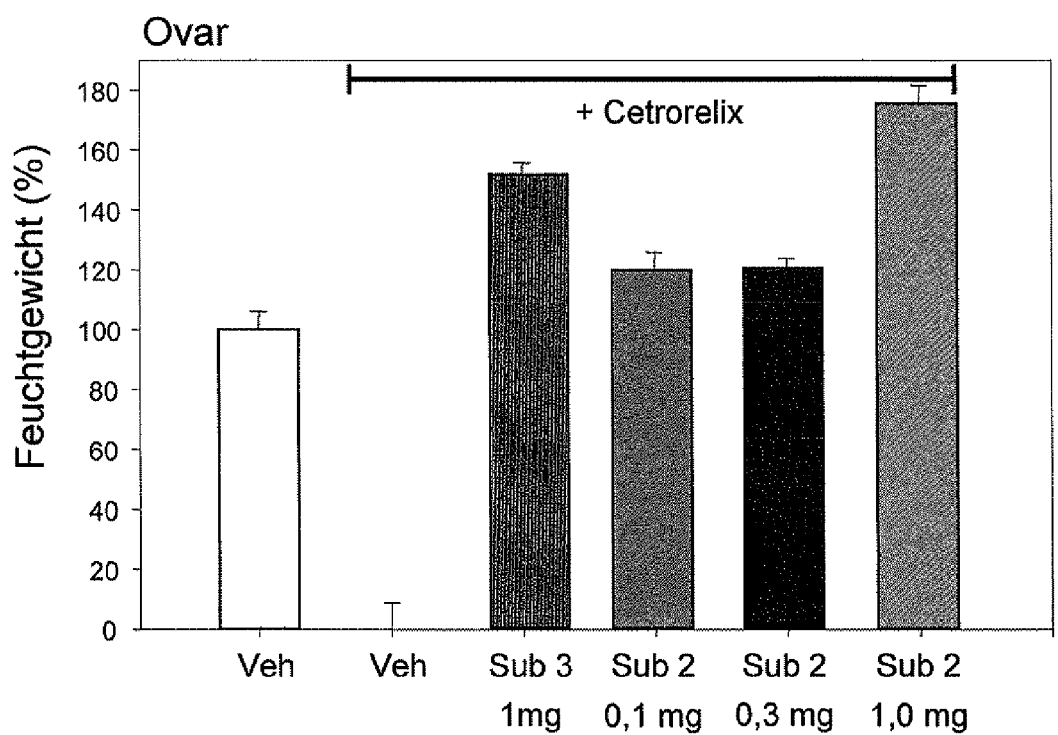
Fig. 1: Change in the ovary weight under the influence of a GnRH antagonist in the treatment with estradiol (Sub3) or various dosages of compound 2

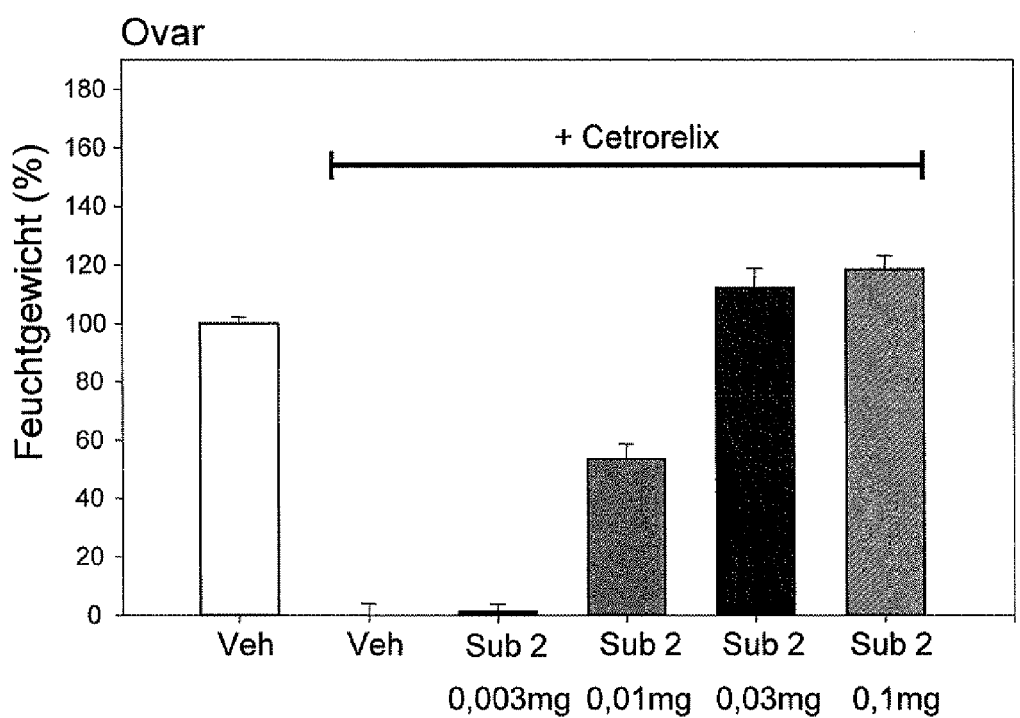
Fig. 2: Positive effect of compound 2 in low dosage on the ovary weight during a combination treatment with the GnRH antagonist Cetrorelix

9-α-SUBSTITUTED ESTRATRIENES AS SELECTIVELY ACTIVE ESTROGENS

FIELD OF THE INVENTION

This invention relates to new compounds as pharmaceutical active ingredients, which have in vitro a higher affinity to estrogen receptor preparations from rat prostates than to estrogen receptor preparations from rat uteri and in vivo a preferential action in the ovary in comparison to the uterus, their production, their therapeutic use and pharmaceutical dispensing forms that contain the new compounds.

The chemical compounds are new, steroidal, tissue-selective estrogens.

BACKGROUND OF THE INVENTION

The efficiency of estrogens in the treatment of hormone-deficiency-induced symptoms such as hot flashes, atrophy of estrogen target organs and incontinence, as well as the successful use of estrogen therapies for prevention of bone mass loss in peri- and postmenopausal women, is well documented and generally accepted (Grady et al. 1992, Ann Intern Med 117:1016-1037). It is also well documented that estrogen replacement therapy in postmenopausal women or in women with ovarian dysfunction that is caused in some other way reduces the risk of cardiovascular diseases compared to women who are not treated with estrogen (Grady et al., loc. cit.).

In conventional estrogen or hormone replacement therapy (=HRT), natural estrogens, such as estradiol, and conjugated estrogens that consist of equine urine are used either by themselves or in combination with a gestagen. Instead of the natural estrogens, derivatives that are obtained by esterification, such as, e.g., 17β-estradiol-valerate, can also be used.

Because of the stimulating action of the estrogens that are used on the endometrium, which results in an increase of the risk of endometrial carcinoma (Harlap, S. 1992, Am J Obstet Gynecol 166:1986-1992), estrogen/gestagen combination preparations are preferably used in hormone replacement therapy. The gestagenic component in the estrogen/gestagen combination avoids hypertrophy of the endometrium, but the occurrence of undesirable intracyclic menstrual bleeding is also linked to the gestagen-containing combination.

Selective estrogens represent a more recent alternative to the estrogen/gestagen combination preparations. Up until now, selective estrogens have been defined as those compounds that have an estrogen-like effect on the brain, bones and vascular system, owing to their antiuterotropic (i.e., antiestrogenic) partial action, but they do not have a proliferative effect on the endometrium.

A class of substances that partially meet the desired profile of a selective estrogen is the so-called "Selective Estrogen Receptor Modulators" (SERM) (R. F. Kauffman, H. U. Bryant 1995, DNAP 8 (9):531-539). In this case, these are partial agonists of estrogen receptor subtype "ERα." This substance type is ineffective, however, with respect to the therapy of acute postmenopausal symptoms, such as, e.g., hot flashes. As an example of a SERM, the raloxifene that was recently introduced for the indication of osteoporosis can be mentioned.

For the treatment of fertility disorders of women, frequently caused by ovarian dysfunction that is caused by surgery, medication, etc., new possible therapies are also opened up by the use of new selective estrogens. The in-vitro fertility treatment is a process that has been established for more than 20 years. Numerous methods for treating ovarian-induced infertility with exogenic gonadotropins are known. By administration of gonadotropins such as FSH (FSH=follicle-stimulating hormone), a stimulation of the ovaries, which is to make possible a healthy follicular maturation, is to be produced.

The follicle is the functional unit of the ovary and has two purposes: it accommodates the oocytes and provides for the latter the possibility for growth and for maturation. Folliculogenesis comprises the development of an ovarian follicle from a primordial stage to a continuously increasing antral follicle, which represents the last stage before ovulation. Only an optimally developed antral follicle can release a mature ovocyte by ovulation.

Patients with ovarian-induced infertility (PCOS=syndrome of polycystic ovaries) suffer from a disrupted follicular maturation, which is associated both with hormonal and ovulatory disruptions and with inadequately matured ovocytes. The number of primary and secondary follicles is approximately twice as high here as in the normal ovary (Hughesden et al., Obstet. Gynecol. Survey 37, 1982, pp. 59-77).

There are indications that the early development stages of folliculogenesis (which relates to the development of primordial follicles to antral follicles) are gonadotropin-independent. It is not clearly explained how great the influence of known paracrine and autocrine factors is on early folliculogenesis (Elvin et al., Mol. Cell Endocrinol. 13, 1999, pp. 1035-1048; McNatty et al., J. Reprod. Fertil. Suppl. 54, 1999, pp. 3-16).

Gonadotropins such as FSH are mainly involved in the last development stages of folliculogenesis in follicular maturation, i.e., in the development of the early antral follicle to a mature follicle that can undergo ovulation.

The in-vivo and in-vitro infertility is preferably treated with gonadotropins (FSH and antiestrogens) (White et al., J. Clin. Endocrinol. Metab. 81, 1996, pp. 3821-3824). In in-vitro fertilization treatment, oocytes are removed from preovulatory antral follicles to be able to mature in vitro into an ovocyte that can be fertilized. After fertilization and preembryonal development, one to three embryos are implanted in the uterus of the woman.

In many respects, the treatment with exogenic gonadotropins is accompanied by numerous risks and side effects. The greatest risk consists in an overstimulation of the ovaries, which in severe cases can represent a serious danger to life (OHSS=Ovarian Hyperstimulation Syndrome). Other side effects are the high costs of the in-vitro fertility treatment that must be paid by the coupled. Negative side effects such as weight gain, bloatedness, nausea, vomiting and an as yet unknown long-term risk of developing cancer are attributed to the gonadotropin treatment.

One method to avoid the above-mentioned drawbacks and risks is to ensure the maturation and stimulation in vivo of follicular growth in the case of ovarian-induced infertility with a suitable active ingredient before treatment with exogenic gonadotropins begins.

Estrogen Receptor Beta (ERβ)

Several years ago, estrogen receptor β (ERβ) was discovered as a second subtype of the estrogen receptor (Kuiper et al. (1996), Proc. Natl. Acad. Sci. 93:5925-5930; Mosselman, Dijkema (1996) Febs Letters 392:49-53; Tremblay et al. (1997), Molecular Endocrinology 11:353-365). The expression pattern of ERβ differs from that of the ERα (Kuiper et al. (1996), Endocrinology 138:863-870). ERβ thus predominates over ERα in the rat prostate, while ERα predominates over ERβ in the rat uterus. The highest concentrations of ERβ and mRNA were found in the ovaries (Couse et al. Endocrinology 138, 1997, pp. 4612-4613).

Other organ systems with comparatively higher ERβ-expression comprise the bones (Onoe, Y. et al., 1997, Endocrinology 138:4509-4512), the vascular system (Register, T. C., Adams, M. R. 1998, J. Steroid Molec Biol 64:187-191), the urogenital tract (Kuiper, G. J. M. et al. 1997, Endocrinology 138:863-870), the gastrointestinal tract (Campbell-Thopson 1997, BBRC 240:478-483), as well as the testis (Mosselmann, S. et al. 1996 FEBS Lett. 392, 49-53) including the spermatides (Shugrue et al. 1998, Steroids 63:498-504). The tissue distribution suggests that estrogens regulate organ functions via ERβ. The fact that ERβ is functional in this respect also follows by studies in ERα-(ERKO) or ERβ-(βERKO)-knockout mice: ovariectomy produces bone mass loss in ERKO-mice, which can be eliminated by estrogen substitution (Kimbro et al. 1998, Abstract OR7-4, Endocrine Society Meeting, New Orleans). Estradiol in the blood vessels of female ERKO mice also inhibits vascular media and smooth muscle cell proliferation (Iafrati, M. D. et al. 1997, Nature Medicine 3:545-548). These protective actions of estradiol are carried out in the ERKO mouse presumably via ERβ.

The fact that ERα and ERβ have a functionally different action was confirmed after successful production of αERKO and βERKO mice. ERα consequently plays an important role in the adult uterus, in mammary gland tissue, in the negative regulation of the gonadotropin activity, while ERβ is mainly bonded in the processes of ovarian physiology, especially that of folliculogenesis and ovulation (Couse et al., Endocrine Reviews 20, 1999, pp. 358-417).

Observations of βERKO mice provide an indication on a function of ERβ in the prostate and bladder: in the case of older male mice, symptoms of prostate and bladder hyperplasia occur (Krege, J. H. et al. 1998, Proc Natl Acad Sci 95:15677-15682). In addition, female ERKO mice (Lubahn, D. B. et al. 1993, Proc Natl Acad Sci 90:11162-11166) and male ERKO mice (Hess, R. A. et al. 1997, Nature 390:509-512) as well as female βERKO mice (Krege, J. H., 1998, Proc Natl Acad Sci 95:15677-15682) have fertility disorders. Consequently, the important function of estrogens with respect to maintaining testis and ovary functions as well as fertility is confirmed.

It was possible to achieve a selective estrogenic action on specific target organs by subtype-specific ligands based on the different tissue or organ distribution of the two subtypes of the ERs. Substances with a preference for ERβ compared to ERα in the in-vitro receptor binding test were described by Kuiper et al. (Kuiper et al. (1996), Endocrinology 138:863-870). A selective action of subtype-specific ligands of the estrogen receptor on estrogen-sensitive parameters in vivo was not previously shown.

The object of this invention is therefore to prepare compounds that have in vitro a dissociation with respect to the binding to estrogen receptor preparations from rat prostates and rat uteri. The compounds are to show in vitro a higher affinity to estrogen receptor preparations from rat prostates than to estrogen receptor preparations from rat uteri.

The ERβ-specific compounds are to produce in vivo a profertility action in the ovary. At the same time, the compounds are to exhibit a dissociation with respect to ovary action in comparison to uterus action. The compounds according to the invention are to have a certain protective action against hormone-deficiency-induced bone mass loss in comparison to uterus-stimulating action.

In the broader sense, a structure-action relationship, which allows for access to compounds that have the above-formulated pharmacological profile, is to be made available by this invention. The compounds according to the invention are to produce enhanced fertility in the ovary while at the same time affecting the uterus very little in cases of ovarian-associated infertility.

According to the invention, the object above is achieved by the provision of 9α-substituted estra-1,3,5(10)-triene derivatives of general formula I

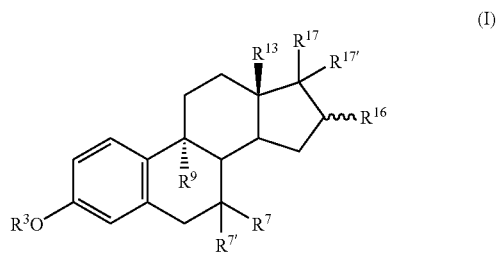

in which radicals $R^3$, $R^7$, $R^{7'}$, $R^9$, $R^{13}$, $R^{16}$ as well as $R^{17}$ and $R^{17'}$, independently of one another, have the following meaning:

$R^3$ means a hydrogen atom or a group $R^{18}$, in which
  $R^{18}$ means a straight-chain or branched-chain, saturated or unsaturated hydrocarbon radical with up to 6 carbon atoms, a trifluoromethyl group, an optionally substituted aryl, heteroaryl or aralkyl radical, an acyl radical $COR^{19}$, in which $R^{19}$ is an optionally substituted, straight-chain or branched-chain hydrocarbon radical with up to 10 carbon atoms that is saturated or unsaturated in up to three places and optionally partially or completely halogenated, or
  $R^{18}$ means a group $R^{20}SO_2$, in which
    $R^{20}$ is an $R^{21}R^{22}N$ group, whereby $R^{21}$ and $R^{22}$, independently of one another, mean a hydrogen atom, a $C_1$-$C_5$-alkyl radical, a group $C(O)R^{23}$, in which $R^{23}$ means an optionally substituted, straight-chain or branched-chain hydrocarbon radical with up to 10 carbon atoms that is saturated or unsaturated in up to three places and is optionally partially or completely halogenated, an optionally substituted $C_3$-$C_7$-cycloalkyl radical, an optionally substituted $C_4$-$C_{15}$-cycloalkylalkyl radical or an optionally substituted aryl, heteroaryl or aralkyl radical, or, together with the N atom, a polymethylenimino radical with 4 to 6 C atoms or a morpholino radical, $R^7$ and $R^{7'}$, in each case independently of one another, are a hydrogen atom or a halogen atom, $R^9$ is a straight-chain or branched-chain alkenyl or alkinyl radical with 2 to 6 carbon atoms, which optionally can be partially or completely fluorinated, $R^{13}$ is a methyl group or an ethyl group, $R^{16}$ is a hydroxy group or a group $R^{18}O$—, $R^{20}SO_2$— or $OC(O)R^{23}$ with $R^{18}$, $R^{20}$ and $R^{23}$ in each case in the meaning that is indicated under $R^3$, $R^{17}$ and $R^{17'}$, in each case independently of one another, are a hydrogen atom or a halogen atom, $R^{16}$ can in each case be in α- or β-position.

According to a variant of the invention, gonatriene derivatives are preferred, in which $R^7$ and $R^{7'}$ are a hydrogen atom, $R^9$ is a vinyl, ethinyl or prop-1-inyl group, $R^{16}$ is a hydroxy group, and $R^{17}$ and $R^{17'}$ in each case are a hydrogen atom.

In addition, the following combinations of halogen substitution, preferably fluorine, in C-atoms 7 and 17 are preferred:

7-mono or 7-di and $R^{17}$ as well as $R^{17'}$, in each case a hydrogen, 17-mono or 17-di and $R^7$ as well as $R^{7'}$, in each case a hydrogen as well as 7-mono/17-mono, 7-mono/17-di, 7-di/17-mono, 7-di/17-di. The 7α-position or the 17β-position is preferred in the monofluorine compounds.

Another variant of the invention in particular calls for compounds in which $R^{16}$ stands for a group $R^{18}O$— or $R^{20}SO_2$—O— with $R^{18}$ and $R^{20}$ in each case in the meaning that is indicated under $R^3$.

Preferred according to this invention are the following compounds:

9α-Vinyl-estra-1,3,5(10)-triene-3,16α-diol
9α-Allyl-estra-1,3,5(10)-triene-3,16α-diol
18a-Homo-9α-vinyl-estra-1,3,5(10)-triene-3,16α-diol
18a-Homo-9α-allyl-estra-1,3,5(10)-triene-3,16α-diol
3-Methoxy-9α-vinyl-estra-1,3,5(10)-trien-16α-ol
9α-Allyl-3-methoxy-estra-1,3,5(10)-trien-16α-ol
18a-Homo-3-methoxy-9α-vinyl-estra-1,3,5(10)-trien-16α-ol
18a-Homo-9α-allyl-3-methoxy-estra-1,3,5(10)-trien-16α-ol
9α-(2',2'-Difluorovinyl)-estra-1,3,5(10)-triene-3,16α-diol
9α-(2',2'-Difluorovinyl)-3-methoxy-estra-1,3,5(10)-trien-16α-ol
16α-Hydroxy-9α-vinyl-estra-1,3,5(10)-trien-3yl-sulfamate
9α-Allyl-16α-hydroxy-estra-1,3,5(10)-trien-3yl-sulfamate
18a-Homo-16α-hydroxy-9α-vinyl-estra-1,3,5(10)-trien-3yl-sulfamate
18a-Homo-9α-allyl-16α-hydroxy-estra-1,3,5(10)-trien-3yl-sulfamate
9α-Vinyl-estra-1,3,5(10)-triene-3,16α-diyl-disulfamate
9α-Allyl-estra-1,3,5(10)-triene-3,16α-diyl-disulfamate
18a-Homo-9α-vinyl-estra-1,3,5(10)-triene-3,16α-diyl-disulfamate
18a-Homo-9α-allyl-estra-1,3,5(10)-triene-3,16α-diyl-disulfamate
16α-Hydroxy-9α-vinyl-estra-1,3,5(10)-trien-3yl-(N-acetyl)-sulfamate
9α-Allyl-16α-hydroxy-estra-1,3,5(10)-trien-3yl-(N-acetyl)-sulfamate
18a-Homo-16α-hydroxy-9α-vinyl-estra-1,3,5(10)-trien-3yl-(N-acetyl)-sulfamate
18a-Homo-9α-allyl-16α-hydroxy-estra-1,3,5(10)-trien-3yl-(N-acetyl)-sulfamate
9α-(Prop-(Z)-enyl)-estra-1,3,5(10)-triene-3,16α-diol
9α-(n-Propyl)-estra-1,3,5(10)-triene-3,16α-diol
9α-Ethinyl-estra-1,3,5(10)-triene-3,16α-diol
9α-Vinyl-estra-1,3,5(10)-triene-3,16α-diol-diacetate
18a-Homo-9α-vinyl-estra-1,3,5(10)-triene-3,16α-diol-diacetate
16α-Valeroyloxy-9α-vinyl-estra-1,3,5(10)-trien-3-ol
16α-Acetoxy-9α-vinyl-estra-1,3,5(10)-trien-3-ol
18a-Homo-16α-acetoxy-9α-vinyl-estra-1,3,5(10)-trien-3-ol
7α-Fluoro-9α-vinyl-estra-1,3,5(10)-triene-3,16α-diol
7α-Fluoro-9α-allyl-estra-1,3,5(10)-triene-3,16α-diol
17β-Fluoro-9α-vinyl-estra-1,3,5(10)-triene-3,16α-diol
17β-Fluoro-9α-allyl-estra-1,3,5(10)-triene-3,16α-diol
18a-Homo-7α-fluoro-9α-vinyl-estra-1,3,5(10)-triene-3,16α-diol
18a-Homo-7α-fluoro-9α-allyl-estra-1,3,5(10)-triene-3,16α-diol
18a-Homo-17β-fluoro-9α-vinyl-estra-1,3,5(10)-triene-3,16α-diol
18a-Homo-17β-fluoro-9α-allyl-estra-1,3,5(10)-triene-3,16α-diol Other possible configurations of this invention will emerge from the subclaims.

Hydrocarbon radical $R^{18}$ is, for example, a methyl, ethyl, propyl, isopropyl, butyl, isobutyl, tert.-butyl, pentyl, isopentyl, neopentyl, or hexyl radical.

Alkoxy groups $OR^{18}$ in the compounds of general formula I in each case can contain 1 to 6 carbon atoms, whereby methoxy, ethoxy, propoxy, isopropoxy and 1-butyloxy groups are preferred.

Representatives of the $C_1$-$C_5$-alkyl radicals $R^{21}$ and $R^{22}$ are methyl, ethyl, propyl, isopropyl, butyl, isobutyl, tert-butyl, pentyl, isopentyl and neopentyl.

As representatives of straight-chain or branched-chain hydrocarbon radicals $R^{22}$ with 1 to a maximum of 10 carbon atoms, for example, methyl, ethyl, propyl, isopropyl, butyl, isobutyl, tert-butyl, pentyl, isopentyl, neopentyl, heptyl, hexyl, and decyl can be mentioned; methyl, ethyl, propyl and isopropyl are preferred.

As a $C_3$-$C_7$-cycloalkyl group, a cyclopropyl, cyclobutyl, cyclopentyl, cyclohexyl or cycloheptyl group can be mentioned.

A $C_4$-$C_{15}$-cycloalkylalkyl radical has 3 to 7 carbon atoms in the cycloalkyl portion; typical representatives are the cycloalkyl groups that are mentioned directly above. The alkyl portion has up to 8 carbon atoms.

As examples of a $C_4$-$C_{15}$-cycloalkylalkyl radical, the cyclopropylmethyl, cyclopropylethyl, cyclopentylmethyl, cyclopentylpropyl groups, etc., can be mentioned.

In terms of this invention, an aryl radical is a phenyl, 1- or 2-naphthyl radical; the phenyl radical is preferred.

Aryl always also includes a heteroaryl radical. Examples of a heteroaryl radical are the 2-, 3- or 4-pyridinyl, the 2- or 3-furyl, the 2- or 3-thienyl, the 2- or 3-pyrrolyl, the 2-, 4- or 5-imidazolyl, the pyrazinyl, the 2-, 4- or 5-pyrimidinyl or 3- or 4-pyridazinyl radical.

As substituents that can be present on an aryl or heteroaryl radical, for example, a methyl-, ethyl-, trifluoromethyl-, pentafluoroethyl-, trifluoromethylthio-, methoxy-, ethoxy-, nitro-, cyano-, halogen- (fluorine, chlorine, bromine, iodine), hydroxy-, amino-, mono($C_{1-8}$ alkyl) or di($C_{1-8}$ alkyl)amino, whereby both alkyl groups are identical or different, di)aralkyl)amino, whereby both aralkyl groups are identical or different, carboxyl, carboxyalkoxy, $C_1$-$C_{20}$-acyl or $C_1$-$C_{20}$-acyloxy groups can be mentioned.

An aralkyl radical is a radical that contains in the ring up to 14, preferably 6 to 10, C atoms, and in the alkyl chain 1 to 8, preferably 1 to 4, C atoms. Thus, as aralkyl radicals, for example, benzyl, phenylethyl, naphthylmethyl, naphthylethyl, furylmethyl, thienylethyl, and pyridylpropyl are suitable.

The alkyl groups or hydrocarbon radicals can be partially or completely substituted by 1-5 halogen atoms, hydroxy groups or $C_1$-$C_4$-alkoxy groups.

A vinyl or allyl radical is primarily defined with a $C_2$-$C_6$-alkenyl radical.

A $C_2$-$C_6$-alkinyl radical is preferably defined as an ethinyl radical or a prop-1-inyl radical.

$C_{1-10}$-Acyl radicals mean, for example, acetyl, propionyl, butyryl, valeroyl, isovaleroyl, pivaloyl, hexanoyl, octyl, nonyl, or decanoyl.

One or two hydroxyl groups at C atoms 3 and 16 can be esterified with an aliphatic, straight-chain or branched-chain, saturated or unsaturated $C_1$-$C_{14}$-mono- or polycarboxylic acid or an aromatic carboxylic acid.

Suitable as such carboxylic acids for esterification are, for example:

Monocarboxylic acids: formic acid, acetic acid, propionic acid, butyric acid, isobutyric acid, valeric acid, isovaleric acid, pivalic acid, lauric acid, myristic acid, acrylic acid, propionic acid, methacrylic acid, crotonic acid, isocrotonic acid, oleic acid, and elaidic acid.

Esterification with acetic acid, valeric acid or pivalic acid is preferred.

Dicarboxylic acids: oxalic acid, malonic acid, succinic acid, glutaric acid, adipic acid, pimelic acid, suberic acid, azelaic acid, sebacic acid, maleic acid, fumaric acid, muconic acid, citraconic acid, and mesaconic acid.

Aromatic carboxylic acids: benzoic acid, phthalic acid, isophthalic acid, terephthalic acid, naphthoic acid, o-, m- and p-toluic acid, hydratropic acid, atropoic acid, cinnamic acid, nicotinic acid, and isonicotinic acid.

Esterification with benzoic acid is preferred.

As prodrugs, the esters of the 9α-substituted estratrienes according to the invention have advantages compared to the unesterified active ingredients with respect to their method of administration, their type of action, strength and duration of action.

Especially the sulfamates of 9α-substituted estratrienes according to the invention have pharmacokinetic and pharmacodynamic advantages. Related effects were already described in other steroid-sulfamates (J. Steroid Biochem. Molec. Biol, 55, 395-403 (1995); Exp. Opinion Invest. Drugs 7, 575-589 (1998)).

In this patent application, steroids on which the 9α-substituted estra-1,3,5(10)-triene skeleton is based are described for the treatment of estrogen receptor β-mediated disorders and conditions as selective estrogens, which have in-vitro dissociation with respect to their binding to estrogen receptor preparations from rat prostates and rat uteri and which have in vivo preferably a dissociation with respect to ovary action in comparison to uterus action. In addition, the compounds have a certain protective action against hormone-deficiency-induced bone mass loss.

It was found that the 9α-substituted estra-1,3,5(10)-trienes according to general formula I are suitable as selective estrogens for the treatment of various conditions and disorders that are characterized by a higher content of estrogen receptor β than estrogen receptor α in the corresponding target tissue or target organ.

The invention also relates to pharmaceutical preparations that contain at least one compound of general formula I (or physiologically compatible addition salts with organic and inorganic acids thereof) and the use of the compounds of general formula I for the production of pharmaceutical agents, especially for the indication mentioned below.

The new selective estrogens that are described here can be used as individual components in pharmaceutical preparations or in combination especially with gestagens. Especially preferred is the combination of selective estrogens with ERα-selective antiestrogens that are peripherally-selectively active, i.e., that do not pass through the blood-brain barriers, as well as with selective estrogen receptor modulators (SERM). The ERβ-selective compounds according to the invention can be used in particular for the production of pharmaceutical agents for treating fertility disorders, for prevention and therapy of prostate hyperplasia, for prevention and treatment of hormone-deficiency-induced mood swings in women and men and for use in hormone replacement therapy (HRT) in men and women.

A therapeutic product that contains an estrogen and a pure antiestrogen for simultaneous, sequential or separate use for the selective estrogen therapy of perimenopausal or postmenopausal conditions is already described in EP-A 0 346 014.

Because of their dissociation of action in the ovary in comparison to the action of the uterus, the substances and the pharmaceutical agents that contain them are especially suitable for the treatment in the case of ovarian dysfunction that is caused by surgery, medication, etc., such as female infertility for stimulation of folliculogenesis for treatment by itself in terms of enhanced fertility, for supporting in-vitro fertility treatment (IVF) in connection with an in-vivo treatment and for treatment of ovarian-induced disorders in later age ("late fertility") as well as for treatment of hormone-deficiency-induced symptoms.

The substances are also suitable for therapy of ovarian diseases such as polycystic ovarian syndrome, POF (premature ovarian failure) syndrome, and ovulation disorders.

Finally, the compounds of general formula I can be used in connection with selective estrogen receptor modulators (SERM) or raloxifene, specifically in particular for use in hormone replacement therapy (HRT) and for treatment of gynecological disorders.

The substances are also suitable as individual components for the treatment of perimenospausal and postmenopausal symptoms, in particular hot flashes, sleep disturbances, irritability, mood swings, incontinence, vaginal atrophy and hormone-deficiency-induced mental disorders. The substances are also suitable for hormone substitution and for the therapy of hormone-deficiency-induced symptoms in ovarian dysfunction that is caused by surgery, medication, etc.

In addition, the substances can also be used to prevent hormone-deficiency-induced bone mass loss and osteoporosis, to prevent cardiovascular system diseases, in particular vascular diseases such as arteriosclerosis, high blood pressure and to prevent hormone-deficiency-induced neurodegenerative diseases, such as Alzheimer's disease, as well as hormone-deficiency-induced impairment of memory and learning capacity.

In addition, the substances can be used as active ingredients in preparations for treating inflammatory diseases and diseases of the immune system, in particular autoimmune diseases, such as, e.g., rheumatoid arthritis, multiple sclerosis, lupus, Crohn's disease and other inflammatory intestinal diseases, inflammatory diseases of the skin, such as psoriasis, as well as for treating endometriosis.

In addition, the substances are effective against inflammatory diseases of the respiratory system, the lungs and bronchial tubes, such as, e.g., asthma.

The medication is suitable for therapy and prophylaxis of estrogen-deficiency-induced diseases both in women and in men.

In men, the compounds are especially suitable for therapy of hormone-deficiency-induced bone mass loss and osteoporosis, for prevention of cardiovascular diseases, in particular vascular diseases such as arteriosclerosis, high blood pressure and for prevention of hormone-deficiency-induced neurodegenerative diseases, such as Alzheimer's disease, as well as hormone-deficiency-induced impairment of memory and learning capacity, and are suitable for prevention and therapy of prostate hyperplasia.

The substances can be used for prophylaxis and therapy of age-related dysfunctions or diseases of men. In particular, they can be used for prevention and treatment of an age-related drop of androgens, such as testosterone and DHEA, as well as of the growth hormone.

In addition, the medication can be used for treating inflammatory diseases and diseases of the immune system, in particular autoimmune diseases in men, such as, e.g., rheumatoid arthritis, MS (multiple sclerosis) and Crohn's disease and other inflammatory intestinal diseases, as well as inflammatory diseases of the respiratory system, the lungs, and the bronchial tubes. The amount of a compound of general formula I that is to be administered fluctuates within a wide range and can cover any effective amount. On the basis of the condition that is to be treated and the type of administration, the amount of the compound that is administered can be 0.01 µg/kg—100 mg/kg of body weight, preferably 0.04 µg/kg—1 mg/kg of body weight, per day.

In humans, this corresponds to a dose of 0.8 µg to 8 g, preferably 3.2 µg to 80 mg, daily.

According to the invention, a dosage unit contains 1.6 µg to 2000 mg of one or more compounds of general formula I.

The compounds according to the invention and the acid addition salts are suitable for the production of pharmaceutical compositions and preparations. The pharmaceutical compositions or pharmaceutical agents contain as active ingredients one or more of the compounds according to the invention or their acid addition salts, optionally mixed with other pharmacologically or pharmaceutically active substances. The production of the pharmaceutical agents is carried out in a known way, whereby the known and commonly used pharmaceutical adjuvants as well as other commonly used vehicles and diluents can be used.

As such vehicles and adjuvants, for example, those are suitable that are recommended or indicated in the following bibliographic references as adjuvants for pharmaceutics, cosmetics and related fields: Ullmans Encyklopädie der technischen Chemie [Ullman's Encyclopedia of Technical Chemistry], Volume 4 (1953), pages 1 to 39; Journal of Pharmaceutical Sciences, Volume 52 (1963), page 918 ff., issued by Czetsch-Lindenwald, Hilfsstoffe für Pharmazie and angrenzende Gebiete [Adjuvants for Pharmaceutics and Related Fields]; Pharm. Ind., Issue 2, 1961, p. 72 and ff.: Dr. H. P. Fiedler, Lexikon der Hilfsstoffe für Pharmazie, Kosmetik und angrenzende Gebiete [Dictionary of Adjuvants for Pharmaceutics, Cosmetics and Related Fields], Cantor K G, Aulendorf in Württemberg 1971.

The compounds can be administered orally or parenterally, for example intraperitoneally, intramuscularly, subcutaneously or percutaneously. The compounds can also be implanted in the tissue.

For oral administration, capsules, pills, tablets, coated tablets, etc., are suitable. In addition to the active ingredient, the dosage units can contain a pharmaceutically compatible vehicle, such as, for example, starch, sugar, sorbitol, gelatin, lubricant, silicic acid, talc, etc.

For parenteral administration, the active ingredients can be dissolved or suspended in a physiologically compatible diluent. As diluents, very often oils with or without the addition of a solubilizer, a surfactant, a suspending agent or an emulsifying agent are used. Examples of oils that are used are olive oil, peanut oil, cottonseed oil, soybean oil, castor oil and sesame oil.

The compounds can also be used in the form of a depot injection or an implant preparation, which can be formulated so that a delayed release of active ingredient is made possible.

As inert materials, implants can contain, for example, biodegradable polymers, or synthetic silicones such as, for example, silicone rubber. In addition, for percutaneous administration, the active ingredients can be added to, for example, a patch.

For the production of intravaginal systems (e.g., vaginal rings) or intrauterine systems (e.g., pessaries, coils, IUDs, Mirena®) that are loaded with active compounds of general formula I for local administration, various polymers are suitable, such as, for example, silicone polymers, ethylene vinyl acetate, polyethylene or polypropylene.

To achieve better bio-availability of the active ingredient, the compounds can also be formulated as cyclodextrin clathrates. For this purpose, the compounds are reacted with α-, β-, or γ-cyclodextrin or derivatives of the latter (PCT/EP95/02656).

According to the invention, the compounds of general formula I can also be encapsulated with liposomes.

Methods

Estrogen Receptor Binding Studies

The binding affinity of the new selective estrogens was tested in competitive experiments with use of $^3$H-estradiol as a ligand to estrogen receptor preparations from rat prostates and rat uteri. The preparation of prostate cytosol and the estrogen receptor test with prostate cytosol was carried out as described by Testas et al. (1981) (Testas, J. et al., 1981, Endocrinology 109:1287-1289).

The preparation of rat uterus cytosol as well as the receptor test with the ER-containing cytosol were basically performed as described by Stack and Gorski (1985) (Stack, Gorski 1985, Endocrinology 117, 2024-2032) with some modifications as described in Fuhrmann et al. (1995) (Fuhrmann, U. et al. 1995, Contraception 51:45-52).

The substances that are described here have higher binding affinity to the estrogen receptor of rat prostates than to estrogen receptors of rat uteri. In this case, it is assumed that ERβ predominates in the rat prostates over ERα, and ERα predominates in rat uteri over ERβ. Table 1 shows that the ratio of the binding to prostate and uterus receptors qualitatively coincides with the quotient of relative binding affinity (RBA) to human ERβ and ERα of rats (according to Kuiper et al. (1996), Endocrinology 138:863-870) (Table 1).

TABLE 1

| Estrogen | hERα RBA* | hERβ RBA* | ERβ/ ERα | Rat uterus ER(RBA) | Rat prost. ER(RBA) | prost. ER/ uterus ER |
|---|---|---|---|---|---|---|
| Estradiol | 100 | 100 | 1 | 100 | 100 | 1 |
| Estrone | 60 | 37 | 0.6 | 3 | 2 | 0.8 |
| 17α-Estra-diol | 58 | 11 | 0.2 | 2.4 | 1.3 | 0.5 |
| Estriol | 14 | 21 | 1.5 | 4 | 20 | 5 |
| 5-Andro-stene-diol | 6 | 17 | 3 | 0.1 | 5 | 50 |
| Genisteine | 5 | 36 | 7 | 0.1 | 10 | 100 |
| Coumes-trol | 94 | 185 | 2 | 1.3 | 24 | 18 |

*Cited from: Kuiper et al. (1996), Endocrinology 138: 863-870

Table 2 shows the results for 4 of the 9α-vinyl-estra-1,3,5 (10)-triene-3,16α-diol derivatives (compounds 1; 2; 4; 5) according to the invention.

TABLE 2

| Compound | RBA Rat Uterus | RBA Rat Prostate |
|---|---|---|
| 9α-Vinyl-estra-1,3,5(10)-3,16α-diol (1) | 1.2 | 100 |
| 9α-Vinyl-estra-1,3,5(10)-17F-3,16α-diol (2) | 2 | 200 |
| 9α-Di-F-Vinyl-estra-1,3,5(10)-3,16α-diol (4) | 0.2 | 4 |
| 9α-Di-F-Vinyl-estra-1,3,5(10)-13-Methyl-3,16α-diol (5) | 0.2 | 6 |

Compounds 1; 2; 4; 5 according to the invention show a higher binding affinity to the estrogen receptor of rat prostates than to the estrogen receptor of rat uteri.

In addition, the predictability of the prostate-ER versus the uterus-ER test system was confirmed with respect to tissue-selective action by in-vivo studies. Substances with a preference for prostate-ER are dissociated in vivo preferably with respect to ovary and uterus action as well as pituitary gland action in favor of action on the ovary.

Studies for Dissociation of Action of the Ovary/Uterus and Pituitary Gland

The studies with respect to the action on uterus growth and ovulation (indirect effect by influencing the secretion of pituitary gland hormones) are performed on adult female rats (body weight of 220-250 g). The substances are subcutaneously administered four times on four consecutive days. The first administration is carried out in the metestrus. One day after the last administration, the autopsy is carried out. The number of ovocytes in the tube (effect on the ovulation) as well as the uterus weight are determined.

While estradiol produces a dose-dependent ovulation inhibition and an increase in uterus weight with an $ED_{50}$ of 0.004 mg/kg of body weight, substance 1 according to the invention up to a dose of 0.4 mg/kg of body weight does not exert any effect on ovulation and uterus weight.

Ovary Studies

The substances were tested in vivo on hypophysectomized juvenile rats. In a modification of this operative method, a GnRH antagonist is administered to the animals. It is examined whether the substance stimulates follicular proliferation (maturation) in the ovary. The ovary weight is the measurement parameter.

In each case, five animals (body weight 40-50 g) are assigned randomly to the treatment groups. The animals are fed as much as they want with a standard diet (altromin) in Makrolon cages in air-conditioned rooms with a lighting program (10 hours of darkness, 14 hours of light) and are given acidified tap water to drink. For the s.c. administration, the test substance as well as the control substance (estradiol E2) are dissolved in benzylbenzoate/castor oil (1+4 v/v).

Juvenile female rats are either hypophysectomized on day 0 and subcutaneously treated (administration 1×daily) from day 1 to day 4 with estradiol, compound 1 or 2 according to the invention, or subcutaneously treated (administration 1×daily) with a vehicle (castor oil/benzyl benzoate). In the modified version of the method, 0.5 mg/animal/day of Cetrorelix is administered to the animals simultaneously with compound 2 or the vehicle and the control substance estradiol over four days of treatment. In both cases, the animals are sacrificed 24 hours after the last administration, and the ovary weight is determined.

0.5 mg/animal/day of compound 1 that is administered subcutaneously over 4 days produces a comparable increase in ovary weight in hypophysectomized animals like estradiol with a dose of 0.1 mg/animal/day. The vehicle does not produce any effect.

Substance 1 according to the invention thus shows a clear dissociation of action in the ovary in comparison to the uterus action and the pituitary gland action and is excellently suited for the preferred indication, the treatment of female infertility, because of its follicle-stimulating action.

In the GnRH antagonist-treated animals, concentrations of 0.1 and 0.3 mg/animal/day of compound 2 in the ovary already show the same action as the dose of 1 mg/animal/day of estradiol that is used (FIG. 1). Even lower dosages (0.01, 0.03 mg/animal/day) show an ovary action and can eliminate the antagonistic effect of Cetrorelix (FIG. 2).

BRIEF DESCRIPTION OF DRAWINGS

FIG. 1: Illustrates the Change in the ovary weight under the influence of a GnRH antagonist in the treatment with estradiol (Sub3) or various dosages of compound 2

FIG. 2: Illustrates the Positive effect of compound 2 in low dosage on the ovary weight during a combination treatment with the GnRH antagonist Cetrorelix Key to FIG. 1:
Ovar=Ovary
Feuchtgewicht (%)=Moist weight (%)
0,1 mg=0.1 mg
0,3 mg=0.3 mg
1,0 mg=1.0 mg Key to FIG. 2:
Ovar=Ovary
Feuchtgewicht (%)=Moist weight (%)
0,003 mg=0.003 mg
0,01 mg=0.01 mg
0.03 mg=0.03 mg
0,1 mg=0.1 mg Substance 2 according to the invention thus also shows a clearly positive action on the ovary by stimulating the follicular maturation and therefore is also suitable for the treatment of female sub- or infertility.

Production of the Compounds According to the Invention

For the production of the compounds of general formula I according to the invention, primarily two synthesis strategies that can generally be applied are used.

On the one hand, in particular 3,16-protected derivatives of estra-1,3,5(10)-triene-3,16ξ-diols, but also optionally the free diols, can be used for modifications of individual positions of the steroid skeleton.

On the other hand, correspondingly modified estrone analogs, which can be obtained in large numbers in known ways [for a typical synthesis process, see J. Chem. Soc. Perk. 1, 1973, 2095 for C(9); Steroids 54, 1989, 71 for C(7)], include a flexible access to the compounds according to the invention by transposition of oxygen functionality (Z. Chem. 1970, 221) from C(17) to C(16).

For the case of the 3-methyl ether, after the ketone is converted into a sulfonyl hydrazone, the formation of the C(16)-C(17) olefin (Z. Chem. 1970, 10, 221 ff; Liebigs Ann. Chem. 1981, 1973 ff), in which hypobromide is stored in a regio-/stereo-controlled way, is carried out in the simplest case by reaction with phenyl sulfonylhydrazide, in a degradation reaction. Reductive dehalogenation and removal of the protective group of C(3) yield the 16β-alcohol, which can be converted according to known methods into the 16α-epimer.

Another variant for the introduction of the hydroxyl group at C-atom 16 is in the hydroboration of the 16(17)-double bond with sterically exacting boranes. It is known of this reaction that it results in 16-oxidized products (Indian J. Chem. 1971, 9, 287-8). Consequently, the reaction of estra-1,3,5(10), 16-tetraenes with, for example, 9-borabicyclo[3,3, 1]nonane after oxidation with alkaline hydrogen peroxide yields 16α-hydroxyestratrienes. To a lesser extent, the epimeric 16β-hydroxy steroids are formed in this reaction. After the cleavage of the 3-methoxy group, estra-1,3,5(10)-triene-3,16α-diols are obtained. By inversion of the configuration at C-atom 16, e.g., by Mitsunobu reaction (synthesis 1980, 1), in turn the 16β-hydroxyestratrienes are obtained.

For further production possibilities of the C(16)-C(17) olefinic intermediate stage, see also DE 199 06 159 A1.

The introduction of fluorine substituents is carried out via nucleophilic substitution reactions of hydroxyl groups with fluoroamine reagents (Org. React. 1974, 21, 158-173). If the hydroxyl groups are converted into the corresponding tosylates in advance, then the fluorinated compounds are obtained by reaction with tetra-n-butylammonium fluoride (J. Chem. Res. (M) 1979, pp. 4728-4755). Fluorine compounds are also accessible by reaction of corresponding alcohols with diethylamino sulfur trifluoride (DAST) (U.S. Pat. No. 3,976,691). Geminal difluorine compounds are produced, for example, by reaction of carbonyl compounds with sulfur tetrafluoride (U.S. Pat. No. 3,413,321) or diethylamino sulfur trifluoride (DAST) (U.S. Pat. No. 3,979,691).

For synthesis of the 9α-substituted 17β-fluoroestra-1,3,5 (10)-triene-3,16-diols according to the invention, 17-oxo-estra1,3,5(10)-trienes are converted into the 17,17-difluoroestra-1,3,5(10)-trienes (U.S. Pat. No. 3,976,691). The thus accessible 17,17-difluoroestra-1,3,5(10)-trienes are converted by treatment with aluminum oxide into 17-fluoroestra-1,3,5(10),16-tetraene (U.S. Pat. No. 3,413,321). Another possibility for the production of fluoro-olefins exists in the reaction of the corresponding ketones with diethylamino sulfur trifluoride (DAST) in the presence of polar catalysts, such as fuming sulfuric acid (U.S. Pat. No. 4,212,815). The reaction of 17-fluoroestra-1,3,5(10),16-tetraenes with boranes and subsequent oxidation with alkaline hydrogen peroxide yields the 17β-fluoroestra-1,3,5(10)-trien-16α-ols (Org. React. 1963, 13, 1-54).

Access to the 9α-alkenyl- or 9α-alkinyl-substituted estra-1,3,5(10)-triene-3,16α-diols according to the invention is carried out first from the 3,16-dihydroxy-estra-1,3,5(10)-trienes that are protected in 3- and 16-position. By reaction with trimethyl silyl cyanide in the presence of lithium perchlorate, the regio- and stereoselective introduction of a 9α-cyano grouping (Synlett, 1992, 821-2) is carried out. After the protective groups are cleaved, the 9α-cyano compound is converted by reduction first into a 9α-formyl compound and then by a Wittig reaction (Org. React. Vol. 14, 270) into the 9α-alkenyl- or 9α-alkinyl-substituted compound.

The estratriene sulfamates according to the invention are accessible in a way that is known in the art from the corresponding hydroxy steroids by esterification with sulfamoyl chlorides in the presence of a base [Z. Chem. 15, 270-272 (1975); Steroids 61, 710-717 (1996)].

Subsequent acylation of the sulfamate group results in the (N-acyl)sulfamates according to the invention. For the (N-acryl)sulfamates, pharmacokinetic advantages were already detected (cf. DE 195 40 233 A1).

The regioselective esterification of polyhydroxylated steroids with N-substituted and N-unsubstituted sulfamoyl chlorides is carried out after partial protection of those hydroxyl groups that are to remain unesterified. Silyl ethers have turned out to be protective groups with selective reactivity that is suitable for this purpose since these silyl ethers are stable under the conditions of sulfamate formation, and the sulfamate group remains intact when the silyl ether(s) is (are) again cleaved for regeneration of the (residual) hydroxyl group(s) still contained in the molecule (Steroids 61, 710-717 (1996)).

The production of the sulfamates according to the invention with an additional hydroxyl group in the molecule is also possible in that the starting material is suitable hydroxy-steroid ketones. First, depending on the goal, one or more hydroxyl groups that are present are subjected to sulfamoylation. Then, the sulfamate groups optionally can be converted with a desired acyl chloride in the presence of a base into the (N-acyl)sulfamates in question. The now present oxosulfamates or oxo-(N-acyl)sulfamates are converted by reduction into the corresponding hydroxysulfamates or hydroxy-(N-acyl)sulfamates (Steroids 61, 710-717 (1996)). Sodium borohydride and the borane-dimethyl sulfide complex are considered as suitable reducing agents.

The examples below are used for a more detailed explanation of the invention.

Analogously to the degradation of the 9α-vinyl grouping, other compounds of general formula I can be obtained with use of reagents that are homologous to the reagents that are described in the examples.

Etherification and/or esterification of free hydroxy groups is carried out according to the methods that are common to one skilled in the art.

Example 1

9α-Vinylestra-1,3,5(10)-triene-3,16α-diol

Stage 1

9α-Cyano-3-methoxy-estra-1,3,5(10)-trien-16α-yl-acetate

A solution of 2.21 g (9.73 mmol) of 2,3-dichloro-5,6-dicyano-1,4-benzoquinone in 80 ml of methylene chloride is added drop by drop while being stirred to a suspension that consists of 2.13 g (6.49 mmol) of 3-methoxy-estra-1,3,5(10)-trien-16α-yl-acetate, 2.07 ml (16.54 mmol) of trimethylsilyl cyanide and 0.14 g of lithium perchlorate in 100 ml of methylene chloride. The reaction mixture is green in color. After 1 hour of reaction time at room temperature, the mixture is mixed with sodium bicarbonate solution. The separated organic phase is washed with water and concentrated by evaporation in a vacuum. The product mixture is chromatographed on silica gel (cyclohexane/ethyl acetate, 6/1). 0.44 g (21%) of 9α-cyano-3-methoxy-estra-1,3,5(10)-trien-16α-yl-acetate is obtained.

Stage 2

9α-Cyano-3-hydroxy-estra-1,3,5(10)-trien-16α-yl-acetate 7.51 g (50.1 mmol) of sodium iodide and 8.87 ml (70.14 mmol) of trimethylchlorosilane are added to a solution that consists of 0.59 g (1.67 mmol) of 9α-cyano-3-methoxy-estra-1,3,5(10)-trien-16α-yl-acetate in 30 ml of acetonitrile while being stirred in an argon atmosphere. After about 3 hours at 60-70° C., the reaction is completed. The reaction solution is added to sodium hydrogen sulfite solution and extracted with ethyl acetate. The organic phase is washed several times with water, dried on $MgSO_4$ and concentrated by evaporation in a vacuum to the dry state.

The crude product is chromatographed on silica gel (cyclohexane/ethyl acetate, 4/1). 0.43 g (76%) of product is obtained.

Stage 3

3,16α-Dihydroxyestra-1,3,5(10)-triene-9 carbonitrile

At room temperature, 0.43 g (1.27 mmol) of 9α-cyano-3-hydroxy-estra-1,3,5(10)-trien-16α-yl-acetate is stirred for 2 hours with 1.0 g (7.24 mmol) of potassium carbonate in 40 ml of methanol (1% water). Then, the methanol is distilled off in a vacuum, and the organic residue is dissolved in methylene chloride. The organic phase is washed with water and concentrated by evaporation. 3.5 g (93%) of 9α-cyano-estra-1,3,5(10)-triene-3,16α-diol is obtained.

Stage 4

3,16α-Dihydroxyestra-1,3,5(10)-triene-9 carbaldehyde

A suspension that consists of 100 mg (0.34 mmol) of 3,16α-dihydroxyestra-1,3,5(10)-triene-9 carbonitrile in 40 ml of toluene is cooled to about −20° C. while being stirred. After 0.9 ml (1.35 mmol) of diisobutylaluminium hydride is added, the reaction is mixed after about 10 minutes with sodium bicarbonate solution, filtered over Celite, and the filtering adjuvant is extracted again with ethyl acetate. The combined organic phases are washed with water. By concentration by evaporation of the solution in a vacuum, 84.6 mg of a light yellow foam is obtained. The product that is contained in the mixture corresponds to a yield of about 52% of theory and is used without further chromatographic working-up in the next stage.

Stage 5

9α-Vinylestra-1,3,5(10)-triene-3,16α-diol

Under inert-gas atmosphere, 3.1 g (7.9 mmol) of triphenylmethyl phosphonium iodide and 0.24 g (8 mmol) of sodium hydride (80% in paraffin oil) in 20 ml of DMSO in an ultrasound bath are brought to reaction at about 55° C. After 10 minutes, 80 mg (0.16 mmol, about 60%) of 3,16α-dihydroxyestra-1,3,5(10)-triene-9 carbaldehyde is added to the solution, and the mixture is allowed to react for 60 more minutes at about 55° C. in an ultrasound bath. After water is added, it is extracted with ethyl acetate. The collected organic phases are washed with water, and the organic phase is concentrated by evaporation in a vacuum.

The crude product is purified by column chromatography on silica gel (cyclohexane/ethyl acetate, 2/1) and subsequent recrystallization from chloroform. Yield: 24 mg (50%), melting point 88-95° C.

$^1$H-NMR (400 MHz, DMSO-d$_6$, TMS): 9.00 (s, 3-OH); 6.98 (d, J=8.6 Hz, H-1); 6.49 (dd, J=8.6/2.7 Hz, H-2); 6.41 (d, J=2.7 Hz, H-4); 6.25 (dd, J=17.2/10.5 Hz, —CH=CH$_2$); 5.00 (dd, 10.5/1.9 Hz, —CH=CH$_2$); 4.47 (d, 4.69 Hz, 16α-OH); 4.45 (dd, 17.2/1.9 Hz, —CH=CH$_2$); 4.24 (m, 16β-H); 2.68 (m, H-6); 0.69 (s, H-18)

Example 2

9α-Vinyl-18a-homo-estra-1,3,5(10)-triene-3,16α-diol

Stage 1

3,16α-Bis[(perhydropyran-2-yl)oxy]-18a-homo-estra-1,3,5(10)-triene-9-carbonitrile 1.03 g (2.26 mmol) of 3,16α-bis[(perhydropyran-2-yl)oxy]-18a-homo-estra-1,3,5(10)-triene, 48.2 mg (0.45 mmol) of lithium perchlorate and 0.71 ml (5.66 mmol) of trimethylsilyl cyanide and introduced into 10 ml of methylene chloride (molecular sieve) and cooled under inert gas to about −70° C. while being stirred. Then, 0.77 g (3.39 mmol) of 2,3-dichloro-5,6-dicyano-1,4-benzoquinone, dissolved in 65 ml of methylene chloride, is added in drops within 1 hours. After about 1 hour (heating to room temperature), the reaction solution is mixed with sodium bicarbonate solution, and the reaction products are extracted with methylene chloride. The crude product that is obtained by concentration by evaporation of the organic phases is purified by chromatography. After chromatography on silica gel (cyclohexane/ethyl acetate, 4/1), 0.74 g (68% of theory) of product is obtained.

Stage 2

3,16α-Dihydroxy-18a-homo-estra-1,3,5(10)-triene-9-carbaldehyde 1.3 g (2.7 mmol) of 3,16α-bis[(perhydropyran-2-yl)oxy]-18a-homo-estra-1,3,5(10)-triene-9-carbonitrile is dissolved in 40 ml of toluene and mixed at room temperature under inert gas with 7.2 ml (10.8 mmol) of diisobutylaluminum hydride solution (1.5 M in toluene). After a reaction time of 30 minutes, a mixture of 30 ml of methanol and 5 ml of dilute hydrochloric acid (1/1) is added to the reaction solution. The reaction solution is concentrated by evaporation under vacuum, and the residue is taken up in ethyl acetate. The organic phase that is obtained is extracted with water and washed with sodium bicarbonate solution. After the solution is dried, and after concentration by evaporation under vacuum, 0.73 g (86% of theory) of yellow crystals is obtained.

Stage 3

9α-Vinyl-18a-homo-estra-1,3,5(10)-triene-3,16α-diol

Under inert gas atmosphere, 13.7 g (34.8 mmol) of triphenylmethyl-phosphonium iodide and 1.0 g (34.8 mmol) of sodium hydride (about 80% on paraffin oil) in 80 ml of DMSO is brought to reaction in an ultrasound bath at about 50° C. After 30 minutes, 0.73 g (2.3 mmol) of 3,16α-dihydroxy-18a-homo-estra-1,3,5(10)-triene-9-carbaldehyde, dissolved in 10 ml of DMSO, is added to the reaction solution, and the mixture is allowed to react in an ultrasound bath for another 60 minutes. After water is added, it is extracted with ethyl acetate, the organic phase is washed with water, dried and concentrated by evaporation.

The crude product is purified by column chromatography on silica gel (cyclohexane/ethyl acetate, 2/1) and crystallization from chloroform.

Yield: 0.59 g (81% of theory) after chromatography

Melting point: 214-220° C.

$^1$H-NMR (400 MHz, DMSO-d$_6$, TMS): 9.00 (s, 3-OH); 6.96 (d, J=8.6 Hz, H-1); 6.49 (dd, J=8.6/2.7 Hz, H-2); 6.41 (d, J=2.7 Hz, H-4); 6.29 (dd, J=17.2/10.5 Hz, —CH=CH$_2$); 5.00 (dd, J=10.5/1.9 Hz, —CH=CH$_2$); 4.48 (d, J=4.7 Hz, 16α-OH); 4.43 (dd, J=17.2/1.9 Hz, —CH=CH$_2$); 4.18 (m, 16β-H); 2.68 (m, H-6); 0.72 (t, J=6.8 Hz, H-18a)

Example 3

9α-(2',2'-Difluorovinyl)-estra-1,3,5(10)-triene-3,16α-diol

Stage 1

3,16α-Bis[(perhydropyran-2-yl)oxy]-estra-1,3,5(10)-triene-9-carbonitrile

Reaction of 3,16α-bis[(perhydropyran-2-yl)oxy]-estra-1,3,5(10)-triene analogously to Example 1, stage 1 yields 3,16α-bis[(perhydropyran-2-yl)oxy]-estra-1,3,5(10)-triene-9-carbonitrile.

Yield: 58% of theory

Stage 2

3,16α-Dihydroxy-estra-1,3,5(10)-triene-9-carbaldehyde

Reaction of 3,16α-bis[(perhydropyran-2-yl)oxy]-estra-1,3,5(10)-triene-9-carbonitrile analogously to Example 1, stage 2 yields 3,16α-dihydroxy-estra-1,3,5(10)-triene-9-carbaldehyde;

Yield: 83% of theory

Stage 3

9α-(2,2-Difluorovinyl)-estra-1,3,5(10)-triene-3,16α-diol 1.5 ml of dimethoxyethane (molecular sieve), 0.3 ml of pentane and 0.13 ml (0.77 mmol) of diethyl(difluoromethyl)-phosphonate are introduced into a reaction flask that was rendered inert, and cooled to about −75° C. After 0.72 ml (1.07 mmol) of tert-butyllithium (1.5 M in pentane) is added and after 30 minutes of reaction time, 0.14 g (0.31 mmol) of 3,16α-dihydroxy-estra-1,3,5(10)-triene-9-carbaldehyde, dissolved in a mixture of 1.5 ml of dimethoxyethane/0.3 ml of pentane, is added to the reaction solution. The reaction solution is refluxed until the reaction is completed. After being added into cooled ammonium chloride solution, it is extracted with ethyl acetate. The organic phase is concentrated by evaporation under vacuum, the residue is taken up in 5 ml of methanol and mixed with 0.5 ml of dilute hydrochloric acid (1/1). Ethyl acetate is added to the reaction solution, the organic phase is washed with sodium bicarbonate solution and concentrated by evaporation under vacuum. The crude product that is obtenied is purified by column chromatography on silica gel (cyclohexane/ethyl acetate, 2/1).

Yield: 22 mg (21% of theory)

$^1$H-NMR (400 MHz, DMSO-$d_6$, TMS): 9.08 (s, 3-OH); 7.10 (d, J=8.6 Hz, H-1); 6.51 (dd, J=8.6/2.3 Hz, H-2); 6.41 (d, J=2.3 Hz, H-4); 5.76 (dd, J=25.4/10.9 Hz, —CH=CF$_2$); 4.51 (d, J=4.69 Hz, 16α-OH); 4.25 (m, 16β-H); 2.68 (m, H-6); 0.68 (s, H-18)

Example 4

9α-(2',2'-Difluorovinyl)-18a-homo-estra-1,3,5(10)-triene-3,16α-diol

Stage 1

3,16α-Bis[(perhydropyran-2-yl)oxy]-18a-homo-estra-1,3,5(10)-triene-9-carbonitrile Reaction of 3,16α-bis[(perhydropyran-2-yl)oxy]-18a-homo-estra-1,3,5(10)-triene analogously to Example 1, stage 1 yields 3,16α-bis[(perhydropyran-2-yl)oxy]-18a-homoestra-1,3,5(10)-triene-9-carbonitrile.

Yield: 58% of theory.

Stage 2

3,16α-Dihydroxy-18a-homo-estra-1,3,5(10)-triene-9-carbaldehyde

Reaction of 3,16α-bis[(perhydropyran-2-yl)oxy]-18a-homo-estra-1,3,5(10)-triene-9-carbonitrile analogously to Example 1, stage 2 yields 3,16α-dihydroxy-18a-homo-estra-1,3,5(10)-triene-9-carbaldehyde.

Yield: 87% of theory

Stage 3

9α-(2,2-Difluorovinyl)-18a-homo-estra-1,3,5(10)-triene-3,16α-diol

Reaction of 3,16α-dihydroxy-18a-homo-estra-1,3,5(10)-triene-9-carbaldehyde; Reaction conditions and execution of the reaction as well as molar ratios as in the 3$^{rd}$ stage of 9α-(2,2-difluorovinyl)-estra-1,3,5(10)-triene-3,16α-diol.

The crude product is purified by column chromatography on silica gel (cyclohexane/ethyl acetate, 2/1) and crystallization from ethyl acetate.

Yield: 12% of theory

Melting point: 225-232° C.

$^1$H-NMR (400 MHz, DMSO-$d_6$, TMS): 9.06 (s, 3-OH); 7.08 (d, J=8.6 Hz, H-1); 6.50 (dd, J=8.6/2.7 Hz, H-2); 6.41 (d, J=2.7 Hz, H-4); 4.78 (dd, J=21.5/14.8 Hz, —CH=CF$_2$); 4.47 (d, J=4.50 Hz, 16α-OH); 4.18 (m, 16β-H); 2.68 (m, H-6); 0.72 (t, J=6.8 Hz, H-18a)

Example 5

17β-Fluoro-9α-vinyl-estra-1,3,5(10)-triene-3,16α-diol

Stage 1

3,16α-Bis[(perhydropyran-2-yl)oxy]-17β-fluoro-estra-1,3,5(10)-triene-9-carbonitrile Reaction of 3,16α-bis[(perhydropyran-2-yl)oxy]-17β-fluoro-estra-1,3,5(10)-triene analogously to Example 2, stage 1 yields 3,16α-bis[(perhydropyran-2-yl)oxy]-17β-fluoro-estra-1,3,5(10)-triene-9-carbonitrile.

Yield: 45% of theory

Stage 2

3,16α-Dihydroxy-17β-fluoro-estra-1,3,5(10)-triene-9-carbaldehyde

Reaction of 3,16α-bis[(perhydropyran-2-yl)oxy]-17β-fluoro-estra-1,3,5(10)-triene-9-carbonitrile analogously to Example 2, stage 2 yields 3,16α-dihydroxy-17β-fluoro-estra-1,3,5(10)-triene-9-carbaldehyde.

Yield: 83% of theory

Stage 3

17β-Fluoro-9α-vinyl-estra-1,3,5(10)-triene-3,16α-diol

Reaction of 3,16α-dihydroxy-17β-fluoro-estra-1,3,5(10)-triene-9-carbaldehyde analogously to Example 2, stage 3 yields 17β-fluoro-9α-vinyl-estra-1,3,5(10)-triene-3,16α-diol.

The crude product is purified by column chromatography on silica gel (cyclohexane/ethyl acetate, 2/1) and crystallization from chloroform.

Yield: 51% of theory

Melting point: 94-98° C.

$^1$H-NMR (400 MHz, DMSO-$d_6$, TMS): 9.02 (s, 3-OH); 6.97 (d, J=8.2 Hz, H-1); 6.51 (dd, J=8.2/2.7 Hz, H-2); 6.42 (d, J=2.7 Hz, H-4); 6.22 (dd, J=17.2/10.5 Hz, —CH=CH$_2$); 5.09 (d, J=5.5 Hz, 16α-OH); 5.01 (dd, J=10.5/1.9 Hz, —CH=CH$_2$); 4.45 (dd, J=17.2/1.9 Hz, —CH=CH$_2$); 4.35 (dd, J=55.1/4.7 Hz, H-17α); 4.11 (m, 16β-H); 2.68 (m, H-6); 0.79 (d, J=1.9 Hz, H-18)

Example 6

17,17-Difluoro-9α-vinyl-estra-1,3,5(10)-triene-3,16α-diol

Stage 1

3,16α-Bis[(perhydropyran-2-yl)oxy]-17,17-difluoro-estra-1,3,5(10)-triene-9-carbonitrile Reaction of 3,16α-bis[(perhydropyran-2-yl)oxy]-17,17-difluoro-estra-1,3,5(10)-triene analogously to Example 2, stage 1 yields 3,16α-bis[(perhydropyran-2-yl)oxy]-17,17-difluoro-estra-1,3,5(10)-triene-9-carbonitrile.

Yield: 46% of theory

Stage 2

3,16α-Dihydroxy-17,17-difluoro-estra-1,3,5(10)-triene-9-carbaldehyde

Reaction of 3,16α-bis[(perhydropyran-2-yl)oxy]-17,17-difluoro-estra-1,3,5(10)-triene-9-carbonitrile analogously to Example 2, stage 2 yields 3,16α-dihydroxy-17,17-difluoro-estra-1,3,5(10)-triene-9-carbaldehyde.

Yield: 88% of theory

Stage 3

17,17-Difluoro-9α-vinyl-estra-1,3,5(10)-triene-3,16α-diol

Reaction of 3,16α-dihydroxy-17,17-difluoro-estra-1,3,5(10)-triene-9-carbaldehyde analogously to Example 2, stage 3 yields 17,17-difluoro-9α-vinyl-estra-1,3,5(10)-triene-3,16α-diol.

The crude product is purified by column chromatography on silica gel (cyclohexane/ethyl acetate, 2/1) and crystallization from chloroform.

Yield: 75% of theory $^1$H-NMR (400 MHz, CDCl$_3$, TMS): 7.08 (d, J=8.6 Hz, H-1); 6.63 (dd, J=8.6/2.7 Hz, H-2); 6.54 (d, J=2.7 Hz, H-4); 6.23 (dd, J=17.2/10.5 Hz, —CH═CH$_2$); 5.08 (dd, J=10.5/1.9 Hz, —CH═CH$_2$); 4.48 (dd, J=17.2/1.9 Hz, —CH═CH$_2$); 4.44 (m, 16β-H); 2.79 (m, H-6); 0.95 (d, J=1.9 Hz, H-18)

Example 7

9α-(hex-1'-enyl)-estra-1,3,5(10)-triene-3,16α-diol

Stage 1

3,16α-Bis[(perhydropyran-2-yl)oxy]-estra-1,3,5(10)-triene-9-carbonitrile

Reaction of 3,16α-bis[(perhydropyran-2-yl)oxy]-estra-1,3,5(10)-triene analogously to Example 2, stage 1 yields 3,16α-bis[(perhydropyran-2-yl)oxy]-estra-1,3,5(10)-triene-9-carbonitrile.

Yield: 61% of theory

Stage 2

3,16α-Dihydroxy-estra-1,3,5(10)-triene-9-carbaldehyde

Reaction of 3,16α-bis[(perhydropyran-2-yl)oxy]-estra-1,3,5(10)-triene-9-carbonitrile analogously to Example 2, stage 2 yields 3,16α-dihydroxy-estra-1,3,5(10)-triene-9-carbaldehyde.

Yield: 87% of theory

Stage 3

9α-(Hex-1-enyl)-estra-1,3,5(10)-triene-3,16α-diol 8.68 g (20 mmol) of pentyltriphenyl-phosphonium bromide+sodium amide (1 g contains 2.3 mmol of pentyltriphenyl-phosphonium bromide), 0.2 g (0.67 mmol) of 3,16α-dihydroxy-estra-1,3,5(10)-triene-9-carbaldehyde and 30 ml DMSO are introduced into a reaction flask that was rendered inert. The reaction mixture is treated for about 2 hours in an ultrasound bath at 60° C. After the reaction is completed, water is added to the reaction solution. The crude product is isolated by extraction with ethyl acetate, washing of the organic phase with water and concentration by evaporation until a dry state is reached.

The crude product that is obtained is purified by column chromatography on silica gel (cyclohexane/ethyl acetate, 1/1) and crystallization from ethyl acetate.

Yield: 0.18 g (75% of theory) according to chromatography

Melting point: 166-168° C.

$^1$H-NMR (400 MHz, DMSO-d$_6$, TMS): 8.97 (s, 3-OH); 7.08 (d, J=8.6 Hz, H-1); 6.49 (dd, J=8.6/2.7 Hz, H-2); 6.41 (d, J=2.7 Hz, H-4); 5.73 (d, J=12.5 Hz, —CH═CH—CH$_2$—); 5.20 (dt, J=12.5/7.4 Hz, —CH═CH—CH$_2$—); 4.48 (d, J=4.7 Hz, 16α-OH); 4.24 (m, 16β-H); 2.66 (m, H-6); 0.68 (t, J=7.0 Hz, CH$_3$—CH$_2$—); 0.66 (s, H-18)

Example 8

9α-(But-1'-enyl)-estra-1,3,5(10)-triene-3,16α-diol

Stage 1

3,16α-Bis[(perhydropyran-2-yl)oxy]-estra-1,3,5(10)-triene-9-carbonitrile

Reaction of 3,16α-bis[(perhydropyran-2-yl)oxy]-estra-1,3,5(10)-triene analogously to Example 2, stage 1 yields 3,16α-bis[(perhydropyran-2-yl)oxy]-estra-1,3,5(10)-triene-9-carbonitrile.

Yield: 52% of theory

Stage 2

3,16α-Dihydroxy-estra-1,3,5(10)-triene-9-carbaldehyde

Reaction of 3,16α-bis[(perhydropyran-2-yl)oxy]-estra-1,3,5(10)-triene-9-carbonitrile analogously to Example 2, stage 2 yields 3,16α-dihydroxy-estra-1,3,5(10)-triene-9-carbaldehyde.

Yield: 87% of theory

Stage 3

9α-(But-1-enyl)-estra-1,3,5(10)-triene-3,16α-diol 8.68 g (20 mmol) of propyltriphenyl-phosphonium bromide+sodium amide (1 g contains 2.3 mmol of propyltriphenyl-phosphonium bromide), 0.2 g (0.67 mmol) of 3,16α-dihydroxy-estra-1,3,5(10)-triene-9-carbaldehyde and 30 ml of DMSO are introduced into a reaction flask that was rendered inert. The reaction mixture is treated for about 2 hours in an ultrasound bath at 60° C. After the reaction is completed, water is added to the reaction solution. The crude product is isolated by extraction with ethyl acetate, washing of the organic phase with water, and concentration by evaporation until a dry state is reached.

The crude product that is obtained is purified by column chromatography on silica gel (cyclohexane/ethyl acetate, 1/1).

Yield: 0.16 g (73% of theory) after chromatography

Melting point: 140-148° C.

$^1$H-NMR (400 MHz, DMSO-d$_6$, TMS): 8.98 (s, 3-OH); 7.09 (d, J=8.6 Hz, H-1); 6.49 (dd, J=8.6/2.7 Hz, H-2); 6.41 (d, J=2.7 Hz, H-4); 5.70 (d, J=12.5 Hz, —CH═CH—CH$_2$—); 5.19 (dt, J=12.5/7.4 Hz, —CH═CH—CH$_2$—); 4.47 (d, J=4.7 Hz, 16α-OH); 4.24 (m, 16β-H); 2.66 (m, H-6); 0.66 (s, H-18); 0.57 (t, J=7.2 Hz, CH$_3$—CH$_2$—)

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German application No. 102 26 326.4, filed Jun. 11, 2002, and U.S. Provisional Application Ser. No. 60/443,868, filed Jan. 31, 2003, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A 9α-Substituted estra-1,3,5(10)-triene compound of formula I

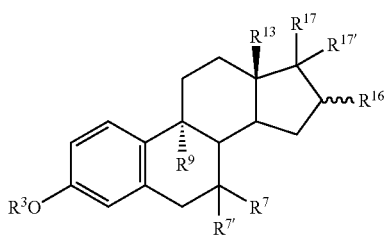

wherein
R³ is hydrogen or R¹⁸,
R¹⁸ is a straight-chain or branched-chain, saturated or unsaturated hydrocarbon radical with up to 6 carbon atoms, a trifluoromethyl group, an optionally substituted aryl, heteroaryl or aralkyl radical, an acyl radical COR¹⁹, or R²⁰SO₂,
R¹⁹ is an optionally substituted, straight-chain or branched-chain hydrocarbon radical with up to 10 carbon atoms that is saturated or unsaturated in up to three places and is optionally partially or completely halogenated,
R²⁰ is R²¹R²²N,
R²¹ and R²² are, independently of one another, a hydrogen atom, a $C_1$-$C_5$-alkyl radical, or C(O)R²³,
R²³ is an optionally substituted, straight-chain or branched-chain hydrocarbon radical with up to 10 carbon atoms that is saturated or unsaturated in up to three places and is optionally partially or completely halogenated, an optionally substituted $C_3$-$C_7$-cycloalkyl radical, an optionally substituted $C_4$-$C_{15}$-cycloalkylalkyl radical or an optionally substituted aryl, heteroaryl or aralkyl radical, or, together with the N atom, a polymethylenimino radical with 4 to 6 C atoms or a morpholino radical,
R¹⁷ and R¹⁷' are, in each case independently of one another, a hydrogen atom or a halogen atom,
R⁹ is a straight-chain or branched-chain alkenyl or alkinyl radical with 2 to 6 carbon atoms, which is optionally partially or completely fluorinated, or an ethinyl or prop-1-inyl radical,
R¹³ is a methyl group or an ethyl group,
R¹⁶ is a hydroxy group or R¹⁸O—, R²⁰SO₂—O— or OC(O)R²³, and
R¹⁷ and R¹⁷' are, in each case independently of one another, a hydrogen atom or a halogen Atom,
or a pharmaceutically acceptable salt thereof.

2. A compound of formula I according to claim 1, in which R³ is a hydrogen atom.

3. A compound of formula I according to claim 1, in which
R⁷ is a hydrogen atom or an α-position fluorine atom,
R⁹ is a vinyl, ethinyl or prop-1-inyl group,
R¹⁶ is a hydroxy group, and
R¹⁷ is a hydrogen atom or an α-position fluorine atom.

4. A compound of formula I according to claim 1, in which R¹⁶ is R¹⁸—O— or R²⁰SO₂—O—.

5. A compound of formula I according to claim 1, which is
9α-Vinyl-estra-1,3,5(10)-triene-3,16α-diol
9α-Allyl-estra-1,3,5(10)-triene-3,16α-diol
18a-Homo-9α-vinyl-estra-1,3,5(10)-triene-3,16α-diol
18a-Homo-9α-allyl-estra-1,3,5(10)-triene-3,16α-diol
3-Methoxy-9α-vinyl-estra-1,3,5(10)-trien-16α-ol
9α-Allyl-3-methoxy-estra-1,3,5(10)-trien-16α-ol
18a-Homo-3-methoxy-9α-vinyl-estra-1,3,5(10)-trien-16α-ol
18a-Homo-9α-allyl-3-methoxy-estra-1,3,5(10)-trien-16α-ol
9α-(2',2'-Difluorovinyl)-estra-1,3,5(10)-triene-3,16α-diol
9α-(2',2'-Difluorovinyl)-3-methoxy-estra-1,3,5(10)-trien-16α-ol
16α-Hydroxy-9α-vinyl-estra-1,3,5(10)-trien-3yl-sulfamate
9α-Allyl-16α-hydroxy-estra-1,3,5(10)-trien-3yl-sulfamate
18a-Homo-16α-hydroxy-9α-vinyl-estra-1,3,5(10)-trien-3yl-sulfamate
18a-Homo-9α-allyl-16α-hydroxy-estra-1,3,5(10)-trien-3yl-sulfamate
9α-Vinyl-estra-1,3,5(10)-triene-3,16α-diyl-disulfamate
9α-Allyl-estra-1,3,5(10)-triene-3,16α-diyl-disulfamate
18a-Homo-9α-vinyl-estra-1,3,5(10)-triene-3,16α-diyl-disulfamate
18a-Homo-9α-allyl-estra-1,3,5(10)-triene-3,16α-diyl-disulfamate
16α-Hydroxy-9α-vinyl-estra-1,3,5(10)-trien-3yl-(N-acetyl)-sulfamate
9α-Allyl-16α-hydroxy-estra-1,3,5(10)-trien-3yl-(N-acetyl)-sulfamate
18a-Homo-16α-hydroxy-9α-vinyl-estra-1,3,5(10)-trien-3yl-(N-acetyl)-sulfamate
18a-Homo-9α-allyl-16α-hydroxy-estra-1,3,5(10)-trien-3yl-(N-acetyl)-sulfamate
9α-(Prop-(Z)-enyl)-estra-1,3,5(10)-triene-3,16α-diol
9α-(n-Propyl)-estra-1,3,5(10)-triene-3,16α-diol
9α-Ethinyl-estra-1,3,5(10)-triene-3,16α-diol
9α-Vinyl-estra-1,3,5(10)-triene-3,16α-diol-diacetate
18a-Homo-9α-vinyl-estra-1,3,5(10)-triene-3,16α-diol-diacetate
16α-Valeroyloxy-9α-vinyl-estra-1,3,5(10)-trien-3-ol
16α-Acetoxy-9α-vinyl-estra-1,3,5(10)-trien-3-ol
18a-Homo-16α-acetoxy-9α-vinyl-estra-1,3,5(10)-trien-3-ol
7α-Fluoro-9α-vinyl-estra-1,3,5(10)-triene-3,16α-diol
7α-Fluoro-9α-allyl-estra-1,3,5(10)-triene-3,16α-diol
17β-Fluoro-9α-vinyl-estra-1,3,5(10)-triene-3,16α-diol
17β-Fluoro-9α-allyl-estra-1,3,5(10)-triene-3,16α-diol
18a-Homo-7α-fluoro-9α-vinyl-estra-1,3,5(10)-triene-3,16α-diol
18a-Homo-7α-fluoro-9α-allyl-estra-1,3,5(10)-triene-3,16α-diol
18a-Homo-17β-fluoro-9α-vinyl-estra-1,3,5(10)-triene-3,16α-diol or
18a-Homo-17β-fluoro-9α-allyl-estra-1,3,5(10)-triene-3,16α-diol.

6. A compound of formula I according to claim 5, which is 17β-Fluoro-9α-vinyl-estra- 1,3,5(10)-triene-3,16α-diol.

7. A pharmaceutical composition comprising a compound according to claim 1 and a pharmaceutically compatible vehicle.

8. A pharmaceutical composition comprising a compound according to claim 5 and a pharmaceutically compatible vehicle.

9. A method for in vitro treatment of female infertility comprising administering to a female in need thereof an effective amount of a pharmaceutical composition according to claim 7.

10. A method for in vivo treatment of female infertility comprising administering to a female in need thereof an effective amount of a pharmaceutical composition according to claim 7.

11. A method for hormone replacement therapy comprising administering to a patient in need of replacement of estrogen, an effective amount of a pharmaceutical composition according to claim 7.

12. A method according to claim 11 further comprising administering to said patient a selective estrogen receptor modulator or raloxifene.

13. A method for therapy of prostate hyperplasia comprising administering to a patient in need thereof an effective amount of a pharmaceutical composition according to claim 7, an antiestrogen and a selective estrogen receptor modulator.

14. A method for treating rheumatoid arthritis comprising administering to a patient in need thereof an effective amount of a pharmaceutical composition according to claim 6.

15. A method for treating multiple sclerosis comprising administering to a patient in need thereof an effective amount of a pharmaceutical composition according to claim 7.

16. A method for treatment of prostate hyperplasia comprising administering to a patient in need thereof an effective amount of a pharmaceutical composition according to claim 7.

17. A method for treatment of a perimenopausal or postmenopausal symptom selected from hot flashes, sleep disturbances, irritability, mood swings, incontinence and vaginal atrophy, comprising administering to a patient in need thereof an effective amount of a pharmaceutical composition according to claim 7.

18. A method according to claim 17, wherein hot flashes are treated.

19. A method according to claim 17, wherein sleep disturbances are treated.

20. A method according to claim 17, wherein irritability is treated.

21. A method according to claim 17, wherein mood swings are treated.

22. A method according to claim 17, wherein incontinence is treated.

23. A method according to claim 17, wherein vaginal atrophy is treated.

24. A method for treatment of prostate hyperplasia comprising administering to a patient in need thereof an effective amount of a pharmaceutical composition according to claim 8.

25. A method for in vitro treatment of female infertility or for in vivo treatment of female infertility or for hormone replacement therapy comprising administering to a female in need thereof an effective amount of a pharmaceutical composition comprising a compound according to claim 6 and a pharmaceutically compatible vehicle.

26. A method for treatment of prostate hyperplasia; rheumatoid arthritis; multiple sclerosis; a perimenospausal or postmenopausal symptom selected from hot flashes, sleep disturbances, irritability, mood swings, incontinence, and vaginal atrophy, comprising administering to a patient in need thereof an effective amount of a pharmaceutical composition comprising a compound according to claim 6 and a pharmaceutically compatible vehicle.

* * * * *

UNITED STATES PATENT AND TRADEMARK OFFICE
CERTIFICATE OF CORRECTION

PATENT NO. : 7,414,043 B2 Page 1 of 1
APPLICATION NO. : 10/458735
DATED : August 19, 2008
INVENTOR(S) : Karl-Heinrich Fritzemeier It is certified that error appears in the above-identified patent and that said Letters Patent is hereby corrected as shown below:

Column 21, line 41, reads "$R^{17}$ and $R^{17}$" should read --$R^7$ and R7'--
Column 21, line 50, reads "Atom" should read0 --atom--
Column 23, line 15, reads "according to claim 6." should read --according to claim 7.--

Signed and Sealed this

Seventeenth Day of March, 2009

JOHN DOLL
*Acting Director of the United States Patent and Trademark Office*